United States Patent
Walker et al.

(10) Patent No.: US 10,770,179 B2
(45) Date of Patent: Sep. 8, 2020

(54) DETERMINING EFFICIENT EXPERIMENTAL DESIGN AND AUTOMATED OPTIMAL EXPERIMENTAL TREATMENT DELIVERY

(71) Applicant: Juntos, Inc., San Carlos, CA (US)

(72) Inventors: Christopher Benjamin Walker, San Francisco, CA (US); Dante Emilio Cassanego, San Carlos, CA (US)

(73) Assignee: JUNTOS, INC., San Carlos, CA (US)

( * ) Notice: Subject to any disclaimer, the term of this patent is extended or adjusted under 35 U.S.C. 154(b) by 866 days.

(21) Appl. No.: 15/442,404

(22) Filed: Feb. 24, 2017

(65) Prior Publication Data
US 2018/0247025 A1    Aug. 30, 2018

(51) Int. Cl.
*G16H 50/20*    (2018.01)

(52) U.S. Cl.
CPC .................................. *G16H 50/20* (2018.01)

(58) Field of Classification Search
CPC ......... G06Q 10/00–50/00; G16H 10/00–80/00
USPC .............................................. 705/7.11–7.42
See application file for complete search history.

(56) References Cited

U.S. PATENT DOCUMENTS

| | | | | |
|---|---|---|---|---|
| 5,520,192 A * | 5/1996 | Kitney | ................ | A61M 16/026 600/529 |
| 6,041,788 A * | 3/2000 | Shen | ...................... | G16H 10/20 128/898 |
| 6,434,511 B1 * | 8/2002 | Stein | ...................... | G06F 17/18 702/113 |
| 6,865,578 B2 * | 3/2005 | Hays | ..................... | G06Q 10/10 |
| 7,080,027 B2 * | 7/2006 | Luby | ..................... | G06Q 10/06 705/7.31 |
| 7,610,153 B2 * | 10/2009 | Carter, Jr. | .............. | G06Q 50/24 702/19 |
| 8,224,665 B2 * | 7/2012 | Morris | .................. | G06F 19/328 705/2 |

(Continued)

OTHER PUBLICATIONS

Herson et al., "The use of interim analysis for sample size adjustment." In: Drug Information Journal, Jul. 1, 1993, 12 pages. Retrieved from <http://journals.sagepub.com/doi/abs/10.1177/009286159302700317?journalCode=dijb>.

(Continued)

*Primary Examiner* — Alan S Miller
(74) *Attorney, Agent, or Firm* — Patent Law Works LLP (57) ABSTRACT

An optimal sample size for experiments targeting units having specific static criteria is determined, based on one or more iterations of a performed experiment. The sample size to use for subsequent experiments targeting units having the specific static criteria is calculated based on target effect of the performed experiment. Multiple iterations can be performed to refine the sample size. Each iteration uses the previously calculated sample size as a parameter. The calculated sample size is then used to determine an optimal treatment. Separate experiments using separate treatments are performed on separate group sets of the calculated sample size. For each separate performed experiment, a score is calculated for the corresponding specific treatment, taking into account actual effect size, statistical significance and homogeneity of effect. Depending upon the score, the given treatment can be accepted for production usage or discarded, or the experiment can be replicated to validate effect.

14 Claims, 3 Drawing Sheets

(56) References Cited

U.S. PATENT DOCUMENTS

| | | | | |
|---|---|---|---|---|
| 8,286,090 B2* | 10/2012 | Ballard | | G06F 3/0481 |
| | | | | 715/781 |
| 8,868,349 B2* | 10/2014 | Cheung | | G16B 40/00 |
| | | | | 702/19 |
| 10,100,359 B2* | 10/2018 | Wu | | C12Q 1/6883 |
| 2003/0065477 A1* | 4/2003 | Opdyke | | G06F 17/18 |
| | | | | 702/179 |
| 2004/0008219 A1* | 1/2004 | Sarel | | A61B 5/0002 |
| | | | | 715/700 |
| 2004/0117239 A1* | 6/2004 | Mittal | | G06Q 30/0201 |
| | | | | 705/7.32 |
| 2004/0132633 A1* | 7/2004 | Carter, Jr. | | G06Q 50/24 |
| | | | | 514/1 |
| 2006/0173663 A1* | 8/2006 | Langheier | | G16H 50/50 |
| | | | | 703/11 |
| 2007/0038475 A1* | 2/2007 | Schlessinger | | G16H 10/20 |
| | | | | 705/2 |
| 2008/0154707 A1* | 6/2008 | Mittal | | G06Q 30/02 |
| | | | | 705/7.33 |
| 2009/0265209 A1* | 10/2009 | Swaminathan | | G06Q 10/06393 |
| | | | | 705/7.13 |
| 2010/0063741 A1* | 3/2010 | Lakatos | | G16H 10/20 |
| | | | | 702/19 |
| 2011/0004442 A1* | 1/2011 | Hathaway | | G06F 3/0484 |
| | | | | 702/179 |
| 2011/0281759 A1* | 11/2011 | Wu | | C12Q 1/6883 |
| | | | | 506/9 |
| 2016/0253469 A1* | 9/2016 | Donovan | | G06F 16/2455 |
| | | | | 705/2 |
| 2016/0292248 A1* | 10/2016 | Garcia | | G06Q 10/067 |
| 2017/0329880 A1* | 11/2017 | Ghosh | | G06F 5/01 |

OTHER PUBLICATIONS

Suckling et al. "Permutation tests for factorially designed neuroimaging experiments." In: Human brain mapping, Apr. 26, 2004, 16 pages. Retrieved from <http://citeseerx.ist.psu.edu/viewdoc/download?doi=10.1.1.420.4289&rep=rep1&type=pdf>.

International Search Report and Written Opinion for PCT/US2018/014538, dated Mar. 19, 2018, 19 pages.

* cited by examiner

DETERMINING EFFICIENT EXPERIMENTAL DESIGN AND AUTOMATED OPTIMAL EXPERIMENTAL TREATMENT DELIVERY

TECHNICAL FIELD

This disclosure pertains generally to statistical determination of the effectiveness of given treatments, and more specifically to calculating optimal sample sizes for experiments targeting units having specific static criteria, and subsequently to optimally determining most effective corresponding treatments.

SUMMARY

A sample size optimization component of a sample size and treatment optimization system determines an optimal sample size for experiments targeting units having specific static criteria. More specifically, the sample size optimization component maintains access to a production set consisting of multiple units. The units are objects that are associated with empirically measurable activity, such that the empirically measurable activity can be influenced by using specific treatments mapped to a specific goal. The units of the production set are exposed to multiple treatments over time, and the corresponding empirical results are measured and tracked. For example, in one embodiment the units comprise people with mobile phones, the treatments comprise text messages, the specific static criteria comprises people having specific demographic criteria and the goal comprises increasing the number of transactions executed.

The sample size optimization component selects, at a specific point in time, a subset of the units of the production set that meet the specific static criteria. The selected subset comprises a given number of units which has been determined for creating a treatment group and a control group. A treatment group of units and a control group of units are then created from the units of the subset, and a paired comparison test is performed on the treatment group and the control group. The paired comparison test compares empirical results against the specific goal over time for the units of the two groups, measured at the specific point in time at which the units were selected from the production set. The groups are accepted only if the mean percentage difference is less than a specific threshold value.

The sample size optimization component also calculates the expected signal-to-noise ratio of the units of the treatment group and the units of control group according to a specific signal-to-noise ratio calculation rule set, taking into account the empirical results for the units of the groups measured at the specific point in time at which the units were selected from the production set. A test of the calculated expected signal-to-noise ratio of the units of the groups is performed, and the groups are accepted only if the expected signal-to-noise ratio exceeds a specific threshold value.

The sample size optimization component records the mean of the control group, the mean of the treatment group, the pairwise standard deviation of the treatment and control groups, and the pairwise mean of the treatment and control groups. An experiment is then performed, in which the units of the treatment group are exposed to a specific treatment whereas the units of control group are not. An effect of the performed experiment is calculated as the mean difference in measured activity between the units of the treatment group and the units of the control group after the experiment has been performed. The calculated effect of the performed experiment is recorded.

At this point, an optimal sample size to use for subsequent experiments targeting units having the specific static criteria is calculated, according to a specific sample size calculation rule set taking into account target effect of the performed experiment and an updated expected signal-to-noise ratio, based on measured empirical results for the units of the groups against the specific goal over time, measured at a second specific point in time occurring after the performing of the experiment. Multiple passes of these steps can be performed, to refine the optimal sample size, wherein each pass uses the previously calculated optimal sample size as a parameter for group creation.

A treatment optimization component of the optimization system scores and selects an optimal treatment targeting units having the specific static criteria. The treatment optimization component receives the calculated optimal sample size to use for experiments targeting units having the specific static criteria. Multiple group sets are created using the steps described above, wherein each group set comprises a treatment group and a control group. Each group is formed according to the received optimal sample size.

A separate experiment using a separate treatment mapped to the specific goal is performed on each separate one of the group sets. For each separate performed experiment, a score is calculated for the corresponding specific treatment, according to a specific score calculation rule set taking into account an actual effect size of the performed experiment, statistical significance of the performed experiment and a measurement of homogeneity of effect of the performed experiment. Depending upon the score for a given treatment, the treatment can be discarded, the experiment using the given treatment can be replicated to validate effect, or the given treatment can be adjudicated as being optimally effective for units with the specific static criteria, and automatically accepted for production usage.

The features and advantages described in this summary and in the following detailed description are not all-inclusive, and particularly, many additional features and advantages will be apparent to one of ordinary skill in the relevant art in view of the drawings, specification, and claims hereof. Moreover, it should be noted that the language used in the specification has been principally selected for readability and instructional purposes, and may not have been selected to delineate or circumscribe the inventive subject matter, resort to the claims being necessary to determine such inventive subject matter.

The Figures depict various embodiments for purposes of illustration only. One skilled in the art will readily recognize from the following discussion that alternative embodiments of the structures and methods illustrated herein may be employed without departing from the principles described herein.

DETAILED DESCRIPTION

Figure 1:
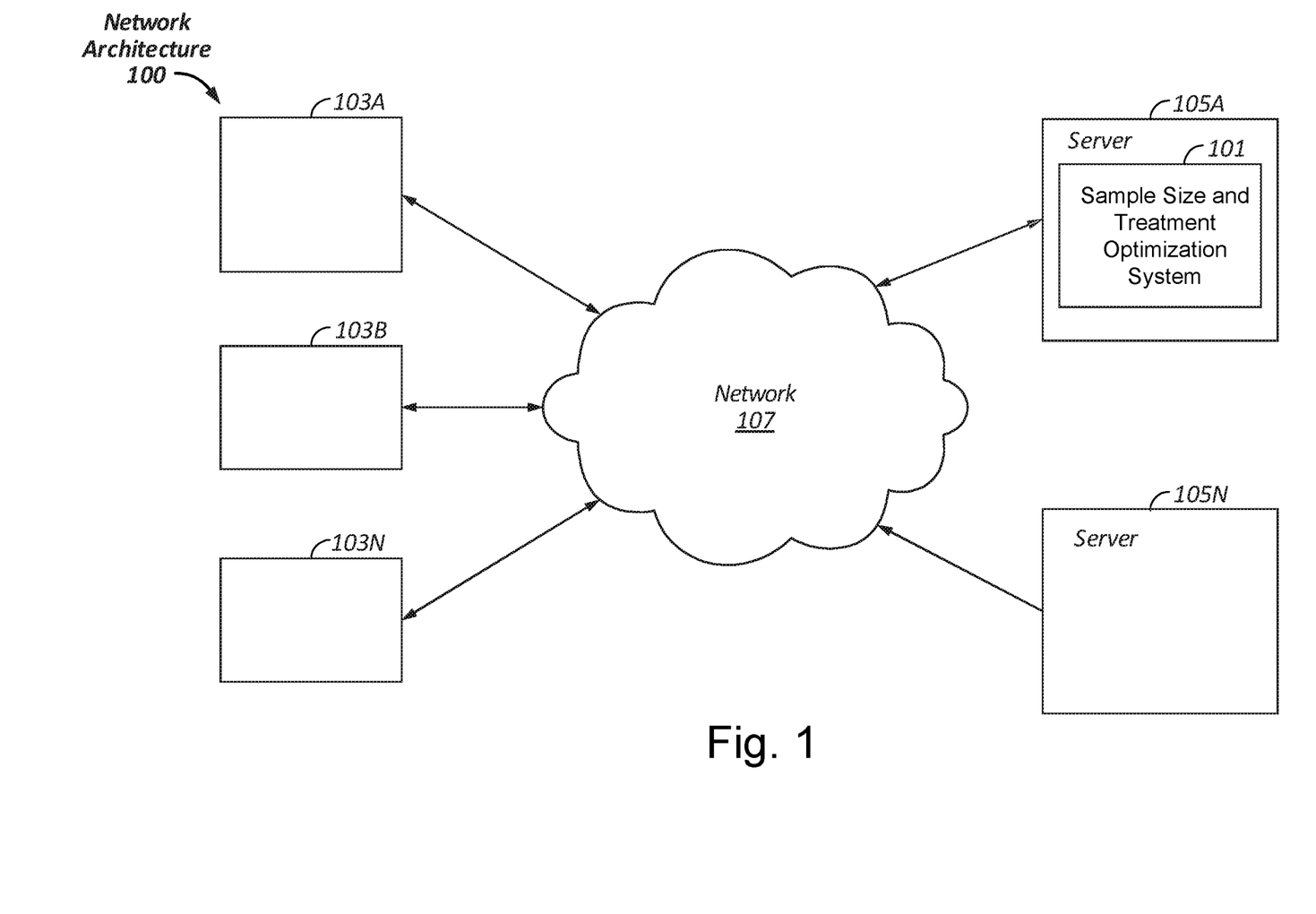
FIG. 1 is a block diagram of an exemplary network architecture in which a sample size and treatment optimization system can be implemented, according to some embodiments.

FIG. 1 is a block diagram illustrating an exemplary network architecture 100 in which a sample size and treatment optimization system 101 can be implemented. The illustrated network architecture 100 comprises multiple clients 103A, 103B and 103N, as well as multiple servers 105A and 105N. Although FIG. 1 illustrates three clients 103 and two servers 105A-N as an example, in practice many more (or fewer) clients 103 and/or servers 105 can be deployed. In one embodiment, the network 107 is in the form of the Internet, although other networks can be used in other embodiments, such as a private enterprise level wide area network.

The clients 103 and servers 105 communicate over the network 107, for example via a network interface 648 or modem 647 as described below in conjunction with FIG. 3. In FIG. 1, a sample size and treatment optimization system 101 is illustrated as residing on server 105A. It is to be understood that this is an example only, and in various embodiments various functionalities of a sample size and treatment optimization system 101 can be instantiated on a client 103, a server 105, or can be distributed between multiple clients 103 and/or servers 105. Clients 103 are able to access applications and/or data on servers 105 using, for example, a web browser or other client software (not shown).

Clients 103 and servers 105 can be implemented using computer systems 610 such as the one illustrated in FIG. 3 and described below. Clients 103 can be in the form of desktop computers, laptop computers, or mobile computing devices, comprising portable computer systems capable of connecting to a network 107 and running applications. Some such mobile computing devices are sometimes referred to as smartphones, although some mobile phones not so designated also have these capabilities. Tablets and wearable computing devices (e.g., smart watches, bracelets, glasses, etc.) are other examples of mobile computing devices.

Figure 2:
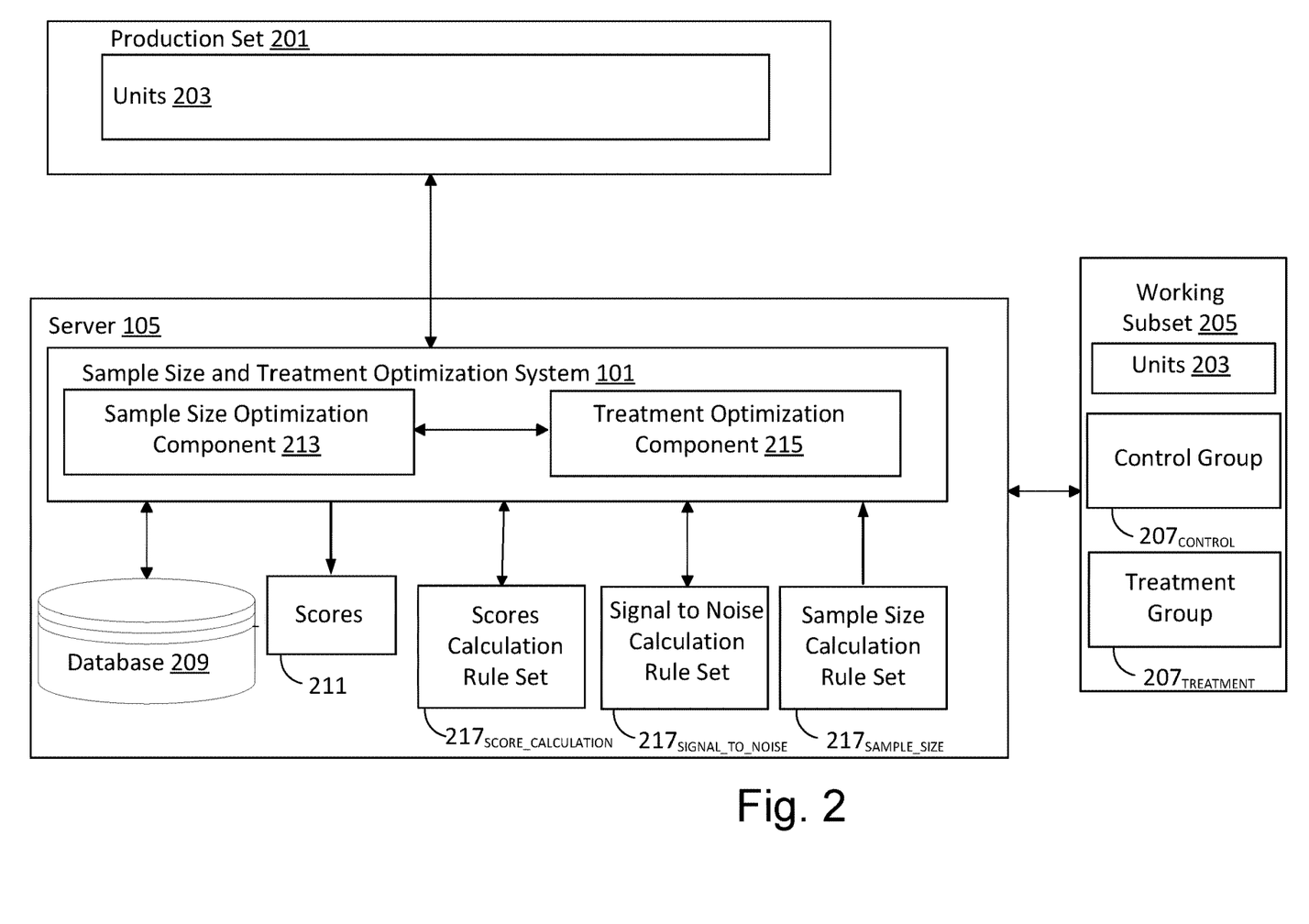
FIG. 2 is a block diagram of the operation of a sample size and treatment optimization system, according to some embodiments.

FIG. 2 illustrates the operation of a sample size and treatment optimization system 101, according to some embodiments. FIG. 2 illustrates a sample size and treatment optimization system 101 residing on a server 105. As described above, the functionalities of the sample size and treatment optimization system 101 can reside on a server 105, a client 103 or be distributed between multiple computer systems 610, including within a cloud-based computing environment in which the functionality of the image security management system 101 is provided as a service over a network 107. It is to be understood that although the sample size and treatment optimization system 101 is illustrated in FIG. 2 as a single entity, the sample size and treatment optimization system 101 represent a collection of functionalities, which can be instantiated as a single or multiple modules as desired. In some embodiments, the different modules of the sample size and treatment optimization system 101 can reside on different computing devices 610 as desired.

It is to be understood that the components and modules of the sample size and treatment optimization system 101 can be instantiated (for example as object code or executable images) within the system memory 617 (e.g., RAM, ROM, flash memory) of any computer system 610, such that when the processor 614 of the computer system 610 processes a module, the computer system 610 executes the associated functionality. As used herein, the terms "computer system," "computer," "client," "client computer," "server," "server computer" and "computing device" mean one or more computers configured and/or programmed to execute the described functionality. Additionally, program code to implement the functionalities of the sample size and treatment optimization system 101 can be stored on computer-readable storage media. Any form of tangible computer readable storage medium can be used in this context, such as magnetic, optical, flash and/or solid state storage media. As used herein, the term "computer readable storage medium" does not mean an electrical signal separate from an underlying physical medium.

As illustrated in FIG. 2, the sample size and treatment optimization system 101 has access to what is referred to herein as a production set 201 of units 203. The units 203 can comprise objects of any type that are associated with empirically measurable activity, such that the empirically measurable activity can be influenced using specific treatment interventions which map to at least one specific goal. For example, in one embodiment the units 203 are in the form of people with mobile phones, being exposed to electronic messages (e.g., text messages, email, etc.) designed to cause them to engage in a specific activity, such as execute a banking transaction. In this example, the treatment interventions are the different electronic messages (e.g., a given treatment could be a specifically worded text message suggesting that the recipient engage in a given transaction, such as transferring funds between accounts electronically). The goal in this scenario would be to maximize the numbers of transfers performed by the units 203 being exposed to the treatment (i.e., the people receiving the text message). The results can be statistically measured by tracking how many transfers each unit performs per period of time (e.g., transfers per month). As the term is used herein, treatment intervention (or treatment) means the procedure, protocol or object applied to the units 203 in an experiment. Of interest is whether the treatment has an effect on the outcome in an attempt to achieve the goal.

It is to be understood that in other embodiments the units can be in other forms, such as, e.g., metal objects being measured for, e.g., hardness after being treated by experimental automatic machine controlled applications of coatings (goal is to increase hardness by some measurable degree, treatment is the parameters used in the specific automatic application of coating), network routers being measured for resistance to malware attacks when being protected by a specific firewall with different configured settings (goal is to increase percentage of attempted attacks that are blocked, treatment is firewall settings), etc.

The units 203 in the production set 201 are subject to one or more treatment(s) over time, and the results are measured against the goal. For example, in the scenario in which the units 203 comprise people with mobile phones and the treatments are in the form of electronic messages suggesting that the recipients engage in banking transactions, actual production treatments (text messages) are sent to the units 203 (people) in the production set 201 over time, and the results are tracked. Thus, at any point in time T, it can be determined how many transactions per period of time (e.g., month, week, day) any given unit 203 has engaged in historically. For example, at a given time, it could be determined how many transactions per month each unit 203 has engaged in for the last six months. In other words, because the units 203 in the production set 201 are being exposed to treatments over time, tracked empirical data exists for the units 203, and can be measured.

It is to be further understood that different units 203 in the product set 201 may have different static criteria. For example, where the units 203 comprise people, different units 203 in the production set 201 can vary by gender (the production set 201 can contain both males and females), physical location (e.g., the production set 201 can contain people located in different countries, different regions of a given country, those who live in cities and those who live in rural areas, etc.), age, profession etc. These criteria can be classified at any level desired of granularity in different embodiments. As used herein "static criteria" means attributes of units 203 that are not being measured for change as a result of exposure to the treatment. This does not necessarily mean that the criteria could never change under any circumstances (e.g., a person could move locations).

In FIG. 2 the production set 201 is illustrated as residing on the same server 105 as the sample size and treatment optimization system 101. It is to be understood that in different embodiments, the production set 201 can reside on other computing and/or storage devices, including on a distributed, cloud based storage architecture.

As described in more detail below, a sample size optimization component 213 of the sample size and treatment optimization system 101 can access units 203 from the production set 201 to determine an optimal sample size for conducting experiments to compare the effectiveness of different treatments on units 203 with specific static criteria (e.g., men ages 18-30 from the South, a specific make of routers versions 3.5-3.7, stainless steel pry bars of lengths 36 to 42 inches, etc.). Once an optimal sample size is determined for a given static criteria segment, a treatment optimization component 215 of the optimization system 101 can in turn run experiments testing different treatments, in order to determine optimally effective treatments for units 203 of that same static criteria segment, in order to achieve a specific goal (e.g., specific text message content that is most effective at causing people with specific demographic criteria to engage in more transactions, specific firewall settings that are most effective in blocking denial of service attacks on a version range of a specific make of routers, etc.).

More specifically, the sample size optimization component 213 of the sample size and treatment optimization system 101 first determines an optimal sample size. To do so, the sample size optimization component 213 selects a first working subset 205 of units 203 meeting a given set of static criteria from the production set 201, at a given first time $T_1$. It is to be understood that the specific static criteria to use can vary as desired, but comprises criteria for which it is desired to learn an optimal treatment to use for achieving a specific goal.

During the first pass through the process described herein for determining optimal sample size, the sample size optimization component 213 assumes an initial sample size $S_{INITIAL}$, which, as explained below, will be experimentally refined in subsequent passes. The specific value to use for $S_{INITIAL}$ is a variable design parameter which can be set according to the nature of the fixed criteria, goal, treatments to be applied, domain knowledge from the relevant literature and/or other factors as desired. The sample size optimization component 213 then selects from the production set 201, at random, a number of units 203 equal to $S_{INITIAL}$ times two plus an overbooking percentage ($S_{INITIAL}$*2+an overbooking %). The initial sample size $S_{INITIAL}$ is multiplied by two so as to create two groups 207 of size $S_{INITIAL}$, a treatment group $207_{TREATMENT}$ and a control group $207_{CONTROL}$. In some embodiments, rather than making two groups 207 through pair matching (as described in detail below), more than two groups 207 are created (e.g., triplets or quadruplets are matched to create three or four groups 207 respectively, depending upon the number of variables, control and/or treatment groups 207 desired, and the nature of the experiment). In such cases, $S_{INITIAL}$*N+the overbooking % units 203 are selected, where N=number of groups 207 to create. The overbooking percentage number of units is added to the total to account for discards to take place after pair matching, which is described below. The specific overbooking percentage to use is a variable design parameter. Units 203 are statistically compared to ensure that the subset 207 is representative of the production set 201.

In an example scenario in which the initial assumed value for the sample size equals 500, two groups 207 are to be created, and the overbooking percentage to use is three, the sample size optimization component 213 would randomly select 500*2+3%=1030 units 203 with the given static criteria from the production set 201. These 1030 units 203 would be placed in first working subset $205_{FIRST}$, at first time $T_1$.

The sample size optimization component 213 next applies pair matching (or matching of larger groupings of units where N>2) to the units 203 in the working subset 205 to make matched pairs (or triplets, quadruplets, Nlets, etc.) to use for the treatment group $207_{TREATMENT}$ and the control group $207_{CONTROL}$. FIG. 2 illustrates a single treatment group $207_{TREATMENT}$ and a single control group $207_{CONTROL}$ although it is to be understood that larger number of groups 207 can be utilized in different embodiments. In the example given above where $S_{INITIAL}$=500 and N=2, the sample size optimization component 213 uses pair matching to create two groups 207, each of which contains 500 units 203. The overbooked units 203 (e.g., the 30 extra units 203 in the example given above) can also be paired to allow for discards as described below. It is to be understood that in different embodiments, different pair matching algorithms (which are an extreme form of the stratified experimental design) can be used. The implementation mechanics of pair matching (including choice of distance measure and input variables) are known to those of ordinary skill in the relevant art, and their use within the context of the operation of the sample size and treatment optimization system 101 will be readily apparent to those of such a skill level in light of this description.

At this stage, the sample size optimization component 213 performs two tests on the groups 207 created by the pair matching, in order to ensure that the groups 207 are statistically suitable. First, the sample size optimization component 213 performs a paired comparison test, based on the empirical results measured at time $T_1$ against the goal for the members of the group over time. For example, take an embodiment in which the results being tracked for the units 203 in the production set 201 are how many transactions per month each unit 203 has engaged in historically. In this embodiment, the paired comparison test could be performed by comparing the mean number of transactions performed in the last month of the treatment group $207_{TREATMENT}$ and the control group $207_{CONTROL}$. In one embodiment, in order to accept these groups 207, the percentage difference of the means between the two groups 207 must be less than a specific threshold value. It is to be understood that the specific threshold value to use is a variable design parameter. Where the percentage difference between the means of the two groups 207 is less than the threshold, the paired comparison test is passed, and the sample size optimization component 213 proceeds to the next test as described below. In one embodiment, where the paired comparison test is not passed, the pair with the greatest difference (e.g., in historical number of transactions per month) is discarded, a new pair from is added from the overbooked units 203, the means of the two groups 207 are recalculated after the pair deletion and addition, and it is determined whether the percentage difference is now below the threshold. In summary, matched pairs can be iteratively discarded to lower the percentage difference of the means between the two groups 207 (and thus improve power). This process is carried out until the paired comparison test is passed or the sample size optimization component 213 runs out of overbooked units 203 in the working subset 205. In case of the later, a new working subset 205 is randomly selected, checked for representation, pair matching is repeated, and the paired comparison test is tried again. In another embodiment, rather than adding a pair from the overbooked units 203, the means of the groups 207 consisting of all the units 203 including those that are overbooked are calculated, and in the event that the percentage difference is not below the threshold, the pair with the greatest difference is discarded, the test repeated, and the process repeated, until either the test is passed or the sizes of the groups 207 drops below a size threshold. The paired comparison test ensures the units 203 in the control and treatment groups 207 are historically similar enough concerning measured activity (e.g., transactions per month).

Once the paired comparison test has been passed, a second test is performed on the groups 207, a test of the expected signal-to-noise ratio. Only if a measurement of the expected signal-to-noise ratio exceeds a specific threshold are the groups 207 considered statistically meaningful enough to be suitable for use in an actual experiment. The expected signal-to-noise ratio is calculated according to a specific signal-to-noise ratio calculation rule set $217_{SIGNAL\_TO\_NOISE}$ which takes into account empirical results for the units 203 of both groups 207 against the specific goal over time. In different embodiments, the expected signal-to-noise ratio can be calculated in different ways. For example, in one embodiment a test referred to herein as the delta ($\delta$) test is performed. The $\delta$ can be calculated according to the formula: mean(treatment group)*(1+expected effect size (%))−mean(control group) standard deviation(pairwise differences)=$\delta$. If $\delta$>threshold, the test is passed, otherwise the test is failed. In other words, the $\delta$ of the two groups 207 is calculated as the mean of the treatment group $207_{TREATMENT}$ multiplied by 1+the expected treatment effect size (in %) minus the mean of the control group $207_{CONTROL}$ all over the standard deviation of the pairwise differences between the units 203 of the two groups. The means of the groups 207 are discussed above. In the example above, the mean of the treatment group is multiplied by 1 plus the expected effect size (%), so that the treatment optimization component 215 takes account of the desired sample size for the future period. Using an expected treatment effect size as an input to the system is known to those of ordinary skill in the art, e.g., in the context of power analysis. The use of this practice within the context of the treatment optimization component 215 will be readily apparent to one of such a skill level in light of this specification.

As for the pairwise differences, the difference (in the measured quantity, e.g., transactions per month) between each unit 201 of the treatment group $207_{TREATMENT}$ and each corresponding (paired) unit 201 of the control group $207_{CONTROL}$ is determined, and the standard deviation of these difference is calculated. The value for the threshold to use is a variable design parameter. If the $\delta$ exceeds the threshold, the measure of the expected signal-to-noise ratio is adjudicated to be sufficient, the test is passed and the treatment and control groups 207 are used for an experiment as described below. In other embodiments, measures of signal-to-noise ratio other than $\delta$ are used for this test.

Once the groups 207 have passed both tests and been designated suitable for use in an experiment, the sample size optimization component 213 records the following values: the mean of the control group, the mean of the treatment group, the pairwise standard deviation, and the pairwise mean. It is to be understood that these values are all calculated based on the measured criteria (e.g., transactions per month) of the units 203 at time $T_1$, when the units were identified in the production set 201, plus a time discount factor can be initially added to the pairwise standard deviation (to account for the increase in time-driven variance). The sample size optimization component 213 can store these values in a database 209 (as illustrated in FIG. 2) or any other suitable storage mechanism or structure.

At this point, an actual experiment can be performed, in which the units 203 in the treatment group $207_{TREATMENT}$ are exposed to a given (e.g., experimental) treatment. At time $T_2$ the experiment treatment effect is calculated as the mean difference in measured activity between the units 203 of the treatment group $207_{TREATMENT}$ and those of the control group $207_{CONTROL}$ which were not exposed to the treatment (e.g., effect of experiment equals mean of treatment group $207_{TREATMENT}$ minus mean of control group $207_{CONTROL}$). In some embodiments, additional variables indicative of the effect of the experiment can also be factored into the calculation. The calculated effectiveness of the experiment is stored in the database 209.

Note that in some embodiments, where the distribution of the units 203 in the working subset 205 is sufficiently bimodal (or multimodal with more than two modes), the working subset 205 is automatically segmented into two (or more) subgroups, and two (or more) separate experiments are conducted using the functionality described above. Since a bimodal distribution is often indicative of two different underlying relationships, running two separate experiments can be more powerful than one. When specifically to segment a working subset 205 is a variable design parameter.

In one embodiment, the sample size optimization component 213 decides when to split a working subset 205 by running several pre-specified splits of those units into further subsets (in the example above, one split would involve splitting the original bimodal distribution into two subsets, another split would involve splitting the original bimodal distribution into three etc.). For each of those pre-specified splits, a standard power analysis is run on each of the new subsets and the results stored. Average power results are then compared across the different splits, and to a power analysis run on the original working subset 205. The pre-specified split is chosen which achieves the highest average power across all subset experiments, under the condition that a threshold number of all the subset experiments are above a given power level. The pre-specified splits, the threshold number of experiments and the given power level are all variable design parameters.

Returning to the main discussion, after a first experiment is conducted and the relevant parameters are stored, the treatment optimization system 101 continues to learn the optimal sample size for running experiments on this given static criteria, with the goal of creating the right conditions to test for the optimal treatment.

In order to continue to learn the optimal sample size for units 203 with the given static criteria, the sample size optimization component 213 executes a subsequent pass of the above described cycle (e.g., at $T_X$ identify units 203 in the production set 201 meeting given static criteria, create a working subset 205 of such units 203, create treatment and control groups 207 of such units, test the groups 207 for statistical suitability, record data measured at a specific time (e.g., $T_X$) concerning the units 203 of the groups 207, run an experiment). However, since an iteration of this cycle has already occurred, the sample size optimization component 213 now has some empirical data on the results of a previous experiment on a working subset 205 of units 203 meeting the given set of static criteria. Thus, rather than assuming a sample size as was done in the first pass, a refined sample size is calculated and used.

The sample size is calculated according to a specific sample size calculation rule set $217_{SAMPLE\_SIZE}$, which takes into account the calculated effect of the performed experiment and an updated expected signal-to-noise ratio. More specifically, in order to calculate the sample size to use for the subsequent iteration, the sample size optimization component 213 calculates a new measurement of expected signal-to-noise ratio (e.g., a new value for $\delta$) for the units 203 making up the treatment and control groups 207 at a new time, $T_2$. Recall that the units 203 that were identified for inclusion in the first working subset 205 and subsequently included in the treatment and control groups 207 are all in the production set 201. In the production set 201, these units are continuing to be subject to production treatments over time to attempt to achieve a goal, and the results are being measured and tracked. Thus, between times $T_1$ and $T_2$, the units 203 of the first working subset 205 that were included in the treatment and control group 207 have also remained in the production set 201, in which capacity they have continued to be exposed to production treatments the results of which are being measured. Thus, at time $T_2$, the sample size optimization component 213 is able to calculate new means for the treatment and control groups 207 of the first working subset 205, as well as a new standard deviation of the pairwise differences between the two groups 207, and thus, with the same expected effect size (again, a variable design parameter) a new $\delta$ (or other quantifier of signal-to-noise ratio) as described above. The new $\delta$ (and means, standard deviation, etc.) can be recorded in the database 209. In this context "new" means current at the new time of calculation, time $T_2$. The interval to use between times of $\delta$ calculations is a variable design parameter which can be adjusted between embodiments as desired (e.g., a month, six weeks, ten days, etc.).

At this point, the sample size optimization component 213 can use a standard statistical power function to solve for the new required sample size $S_{NEW}$ to use in the next pass. More specifically, using a power function of the form power=f (sample size S, measurement of signal-to-noise ratio $\delta$, the target effect size parameter), the sample size optimization component 213 can solve for S using $\delta$ as calculated for time $T_2$, the target effect size parameter and an assumed sufficient power. The value to use for the assumed sufficient power is itself a variable design parameter (e.g., 75%, 80%, 90%, etc.). The exact power function to use is also a variable design parameter. Note, as further experiments are run on the given fixed segment as described below, the target effect size is refined so that the sample size optimization component 213 targets a reasonable effect size in its power analysis. Since there are no guarantees that a given experiment works initially, this target effect size parameter is learned with time, as effective experiments are run.

Using the calculated value for $S_{NEW}$, the sample size optimization component 213 repeats the steps described above to create a new working subset 205 of units 203 meeting the given set of static criteria from the production set 201, at a new time $T_X$, selecting from the production set 201, at random, $S_{NEW}*2$+an overbooking % units 203, to again make a treatment group $207_{TREATMENT}$ and a control group $207_{CONTROL}$. As described above the means, standard deviation and signal-to-noise ratio are calculated, the new groups 207 are subject to the same suitability tests as described above, and once having passed, the same values concerning the units 203 are recorded in the database 209 in a new record associated with the current pass. An experiment is then conducted using the new groups 207 and the same treatment, the same relevant parameters are calculated at new time $T_Y$ and stored. The power function can then be used to calculate a revised sample size S, and another iteration performed.

Thus, each iteration involves creating groups 207 based on a current sample size, determining and storing relevant information concerning the groups 207, conducting an experiment using the new groups 207 and the same treatment, and then calculating and storing the updated relevant information concerning the groups 207. By executing multiple iterations of this process, the value to use for the sample size is refined. Each iteration refines the optimal sample size to use for an experiment involving the given treatment on the particular fixed criteria segment at issue, over a given window of time. In other words, refining the sample size towards optimal exposes the true sample size required to reveal an effect of given size of the given treatment on units 203 having the particular static criteria.

When specifically to break the loop and stop performing iterations can vary between embodiments. Generally, the sample size optimization component 213 stops running iterations using a specific treatment on units 203 having a given static criteria once the calculated sample size is not significantly changing between passes and is stable. Techniques for making such determinations of sample size stability are known to those of ordinary skill in the relevant art, and the implementation of such techniques within the context of the sample size and treatment optimization system 101 will be readily apparent to one of such a skill level in light of this description.

Note that the functionality described above in conjunction with the sample size optimization component 213 is an example of the first major function performed by the sample size and treatment optimization system 101: sample size optimization. Once an optimal sample size for a given segment of fixed static criteria has been determined, the sample size and treatment optimization system 101 executes the second major component of the system, which is to optimize and deliver an optimally effective treatment.

Once a preferred sample size is determined for units 203 having a particular given static criteria, the sample size optimization component 213 can output the sample size to the treatment optimization component 215 of the sample size and treatment optimization system 101, in order to score and select an optimal treatment targeting units having the specific static criteria. The treatment optimization component 215 can create multiple pairs (or triplets, quadruplets, etc.) of groups 207 of this number of units 203 having this criteria, using the functionality described above for creation of the groups 207. The treatment optimization component 215 can then use the created sets of groups 207 of the empirically determined optimal sample size to perform experiments using different treatments and, after a period of time (or number of cycles) have passed, measure the effect of each different treatment. In other words, to run an experiment with for example, eight different treatments, eight different group sets would be created and assigned one of the eight different treatments. The effect of each of these treatments on groups 207 (containing the optimal sample size number of units 203) is then measured and compared in the next period.

In order to determine and deliver an optimally effective treatment, the treatment optimization component 215 begins by calculating and assigning a score 211 to the given treatment used in each specific experiment undertaken. Since multiple experiments are simultaneously being conducted on a group with given static criteria, scores 211 are compared to determine the most optimal treatment. The score 211 for a given treatment is calculated according to a specific score calculation rule set $217_{SCORE\_CALCULATION}$, taking into account the actual effect size of the experiment utilizing the treatment (e.g., calculated as the difference between the means of the treatment group $207_{TREATMENT}$ and the control group $207_{CONTROL}$), the statistical significance (p-value) and a measurement of the homogeneity of the effect across the treatment group 207.

The p-value is the canonical measurement of statistical significance of the treatment effect. In one embodiment, a Bonferroni adjustment is applied to account for the multiple pairwise tests taking place. To measure the treatment effect homogeneity, the skewness and/or kurtosis (third and fourth statistical moments) can be taken of the pairwise-differences. The exact function used to calculate the score 211 is a variable design parameter and can be adjusted between embodiments. Typically, higher scores 211 are a function of greater observed (normalized) effect sizes, a statistically-significant effect size (p-value below a canonical threshold) and homogeneously-distributed effect sizes. In some embodiments, additional factors indicative of the validity of the experiment can also be utilized in score 211 calculation (e.g. the number of replications/iterations performed of this given experiment/treatment). In one example embodiment, score 211 can be calculated according to the following formula:

$$Score_i = Dir_i(\alpha ES_i + \beta[PValue_i] + \gamma Skew_i + \lambda Kurt_i)$$

$Dir_i$=Indicator for correct effect direction for experiment i
$ES_i$=Standardized absolute effect size for experiment i
$PValue_i$=Bonferroni-adjusted P-value derived from H0: $ES_i$=0
$Skew_i$=Standardized log of the absolute skewness of experimental pairwise differences
$Kurt_i$=Standardized log of the kurtosis of experimental pairwise differences
$(\alpha, \gamma, \lambda)$=Variable design parameters
$\beta$=Step function for P-value thresholds
Standardizations are made across the $\{i=1 \ldots N\}$ experiments simultaneously taking place on the given segment.

Based on the score 211 for a specific treatment utilized in a given experiment, the treatment optimization component 215 can determine whether the treatment is optimal for units 203 with the given static criteria. In one embodiment, if the score 211 is below a given threshold, the treatment is discarded as being suboptimal, and is not used or subject to further experiments. If the score 211 is within a given range (e.g., above a cutoff threshold value but below an acceptance threshold value), the experiment utilizing the treatment is replicated to validate the treatment effect. How many times to replicate the experiment and under what specific conditions are design variables. A treatment that generates a score 211 greater than a specific threshold (e.g., the accept threshold) is adjudicated as being effective for units 203 with the given static criteria, and is automatically accepted, e.g., for actual production usage. What specific values to use for the cutoff threshold and acceptance threshold are variable design parameters.

It is to be understood that treatments adjudicated as being sufficiently effective for units 203 having a given fixed criteria as described above can be automatically released into production usage. For example, in an embodiment in which the units 203 are people, the static criteria are males aged 20-30 from a specific geographic region and the treatment is a specific text message designed to cause them to engage in a specific type of transactions, the text message that generated the score 211 can be automatically delivered and utilized commercially to target members having that demographic. In another embodiment where the units 203 are in the form of metal objects, the static criteria is copper tubing with a given range of diameters and the treatment is a given set of parameters for use when automatically applying a chemical coating designed to increase hardness, the high scoring experiment can be automatically approved and applied in a production environment, or otherwise moved to the next phase in a pipeline process.

In conclusion, it is to be understood that the sample size optimization component 213 of the sample size and treatment optimization system 101 can utilize the above-described functionality to determine optimal samples sizes for different types of units 203 having different static criteria in parallel. Once optimal samples sizes are determined, the treatment optimization component 215 of the sample size and treatment optimization system 101 can then test multiple treatments within one experiment and run multiple experiments for many different demographic groups, or other static criteria segments, comparing the scores 211 across those experiments, determine optimal treatments and automatically administer those optimal treatments targeting different static criteria segments as desired.

Figure 3:
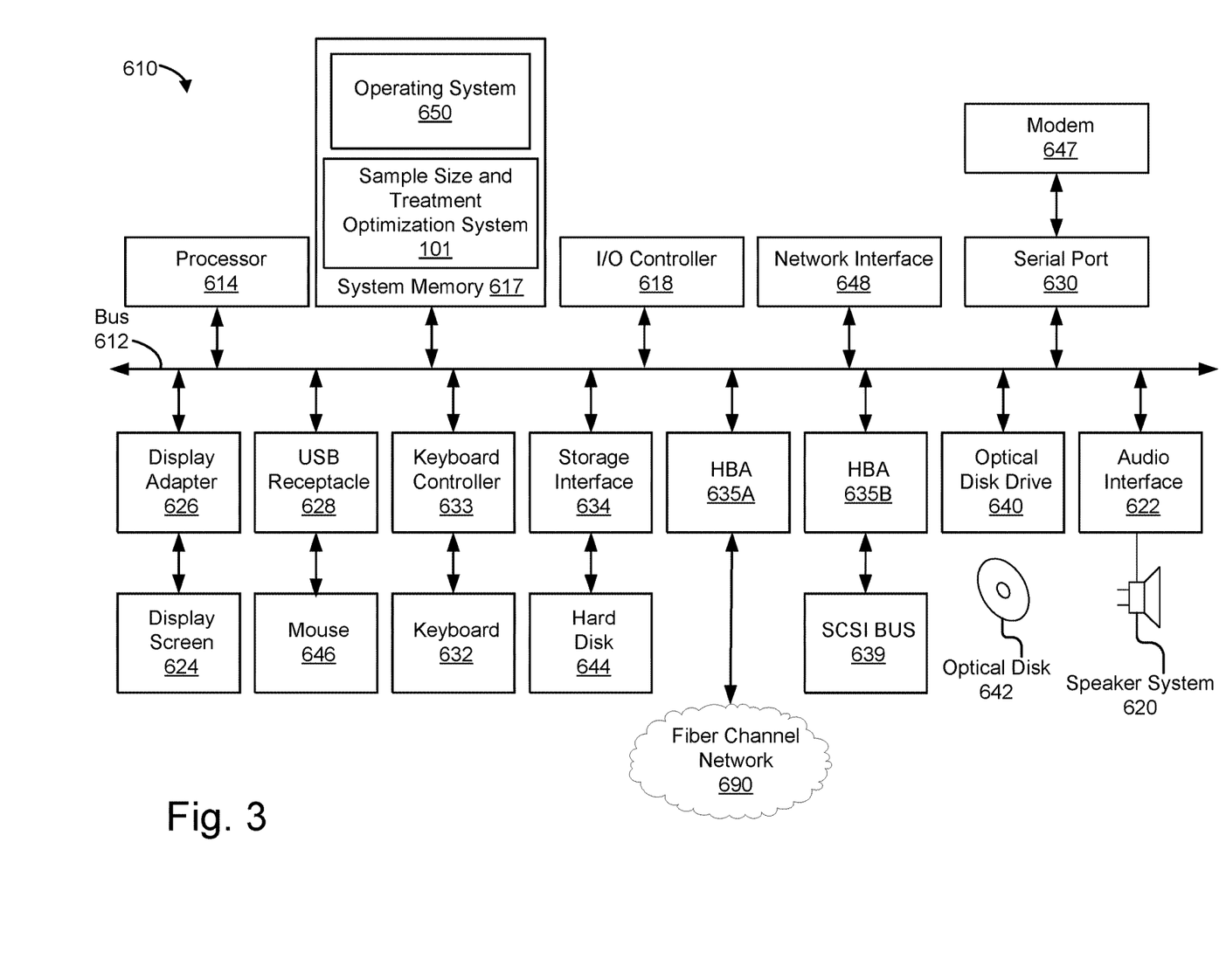
FIG. 3 is a block diagram of a computer system suitable for implementing a sample size and treatment optimization system, according to some embodiments.

FIG. 3 is a block diagram of a computer system 610 suitable for implementing a sample size and treatment optimization system 101. Both clients 103 and servers 105 can be implemented in the form of such computer systems 610. As illustrated, one component of the computer system 610 is a bus 612. The bus 612 communicatively couples other components of the computer system 610, such as at least one processor 614, system memory 617 (e.g., random access memory (RAM), read-only memory (ROM), flash memory), an input/output (I/O) controller 618, an audio output interface 622 communicatively coupled to an audio output device such as a speaker 620, a display adapter 626 communicatively coupled to a video output device such as a display screen 624, one or more interfaces such as Universal Serial Bus (USB) receptacles 628, serial ports 630, parallel ports (not illustrated), etc., a keyboard controller 633 communicatively coupled to a keyboard 632, a storage interface 634 communicatively coupled to one or more hard disk(s) 644 (or other form(s) of storage media), a host bus adapter (HBA) interface card 635A configured to connect with a Fibre Channel (FC) network 690, an HBA interface card 635B configured to connect to a SCSI bus 639, an optical disk drive 640 configured to receive an optical disk 642, a mouse 646 (or other pointing device) coupled to the bus 612, e.g., via a USB receptacle 628, a modem 647 coupled to bus 612, e.g., via a serial port 630, and one or more wired and/or wireless network interface(s) 648 coupled, e.g., directly to bus 612.

Other components (not illustrated) may be connected in a similar manner (e.g., document scanners, digital cameras, printers, etc.). Conversely, all of the components illustrated in FIG. 3 need not be present (e.g., smartphones and tablets typically do not have optical disk drives 640, external keyboards 632 or external pointing devices 646, although various external components can be coupled to mobile computing devices via, e.g., USB receptacles 628). The various components can be interconnected in different ways from that shown in FIG. 3.

The bus 612 allows data communication between the processor 614 and system memory 617, which, as noted above may include ROM and/or flash memory as well as RAM. The RAM is typically the main memory into which the operating system 650 and application programs are loaded. The ROM and/or flash memory can contain, among other code, the Basic Input-Output system (BIOS) which controls certain basic hardware operations. Application programs can be stored on a local computer readable medium (e.g., hard disk 644, optical disk 642) and loaded into system memory 617 and executed by the processor 614. Application programs can also be loaded into system memory 617 from a remote location (i.e., a remotely located computer system 610), for example via the network interface 648 or modem 647. In FIG. 3, the sample size and treatment optimization system 101 is illustrated as residing in system memory 617.

The storage interface 634 is coupled to one or more hard disks 644 (and/or other standard storage media). The hard disk(s) 644 may be a part of computer system 610, or may be physically separate and accessed through other interface systems.

The network interface 648 and/or modem 647 can be directly or indirectly communicatively coupled to a network 107 such as the internet. Such coupling can be wired or wireless.

As will be understood by those familiar with the art, the invention may be embodied in other specific forms without departing from the spirit or essential characteristics thereof. Likewise, the particular naming and division of the portions, modules, agents, managers, components, functions, procedures, actions, layers, features, attributes, methodologies, data structures and other aspects are not mandatory or significant, and the mechanisms that implement the invention or its features may have different names, divisions and/or formats. The foregoing description, for purpose of explanation, has been described with reference to specific embodiments. However, the illustrative discussions above are not intended to be exhaustive or limiting to the precise forms disclosed. Many modifications and variations are possible in view of the above teachings. The embodiments were chosen and described in order to best explain relevant principles and their practical applications, to thereby enable others skilled in the art to best utilize various embodiments with or without various modifications as may be suited to the particular use contemplated.

What is claimed is:

1. A computer implemented method for determining an optimal sample size for experiments targeting units having specific static criteria, the method comprising:

maintaining access, by a computer, to a plurality of units of a production set, wherein the units comprise mobile computing devices that are associated with empirically measurable activity, such that the empirically measurable activity can be influenced by using specific treatments mapped to a specific goal, wherein the production set comprises a plurality of units that are being exposed to a plurality of treatments over time and corresponding empirical results are being measured and tracked, wherein the treatments comprise electronic messages automatically transmitted by a sample size and treatment optimization system to the mobile computing devices;

selecting, by the computer, at a specific point in time, a subset of units of the production set meeting specific static criteria, the selected subset comprising a given number of units, the given number having been determined for creating a treatment group and a control group;

creating, by the computer, a treatment group of units from the subset meeting the specific static criteria and a control group of units from the subset meeting the specific static criteria;

performing, by the computer, a paired comparison test on the treatment group and the control group, wherein the paired comparison test compares empirical results for the units of the treatment group to empirical results for the units of the control group, the empirical results for the units of the treatment group and for the units of control group being against the specific goal over time, measured at the specific point in time at which the units were selected from the production set;

accepting, by the computer, the treatment group and the control group only in response to a mean percentage difference between the treatment group and the control group being less than a specific threshold value;

calculating, by the computer, expected signal-to-noise ratio of the units of the treatment group and the units of control group according to a specific signal-to-noise ratio calculation rule set, taking into account empirical results for the units of the treatment group and for the units of control group against the specific goal over time, measured at the specific point in time at which the units were selected from the production set;

performing, by the computer, a test of the calculated expected signal-to-noise ratio of the units of the treatment group and the units of control group;

accepting, by the computer, the treatment group and the control group only in response to the calculated expected signal-to-noise ratio exceeding a specific threshold value;

recording, by the computer, mean of the control group, mean of the treatment group, pairwise standard deviation of the treatment and control groups, and pairwise mean of the treatment and control groups, calculated based on measured empirical results for the units of the treatment group and for the units of the control group against the specific goal over time, measured at the specific point in time at which the units were selected from the production set;

performing, by the computer, an experiment comprising exposing the units of the treatment group to a specific treatment and not exposing the units of the control group to the specific treatment;

calculating, by the computer, an effect of the performed experiment as mean difference in measured activity between the units of the treatment group and the units of the control group after having performed the experiment;

recording, by the computer, the calculated effect of the performed experiment; and calculating, by the computer, an optimal sample size to use for subsequent experiments targeting units having the specific static criteria, according to a specific sample size calculation rule set taking into account target effect of the performed experiment and an updated expected signal-to-noise ratio, wherein the updated expected signal-to-noise ratio is calculated based on measured empirical results for the units of the treatment group and for the units of the control group against the specific goal over time, measured at a second specific point in time occurring after the performing of the experiment.

2. The method of claim 1 further comprising:

executing at least one additional pass to refine the optimal sample size to use for subsequent experiments targeting units having the specific static criteria, wherein executing an additional pass further comprises:

selecting, by the computer, at a subsequent specific point in time, a new subset of units of the production set meeting the specific static criteria, the selected new subset comprising a given number of units for creating a new treatment group and a new control group, the given number being informed by a most recently previously calculated optimal sample size;

creating, by the computer, a new treatment group of units from the new subset meeting the specific static criteria and a new control group of units from the new subset meeting the specific static criteria;

performing, by the computer, a paired comparison test on the new treatment group and the new control group, wherein the paired comparison test compares empirical results for the units of the new treatment group to empirical results for the units of the new control group, the empirical results for the units of the new treatment group and for the units of the new control group being against the specific goal over time, measured at the subsequent specific point in time at which the new subset of units was selected from the production set;

accepting, by the computer, the new treatment group and the new control group only in response to a mean percentage difference between the new treatment group and the new control group being less than a specific threshold value;

calculating, by the computer, expected signal-to-noise ratio of the units of the new treatment group and the units of the new control group according to the specific signal-to-noise ratio calculation rule set, taking into account empirical results for the units of the new treatment group and for the units of the new control group against the specific goal over time, measured at the specific subsequent point in time at which the new subset of units was selected from the production set;

performing, by the computer, a test of the calculated expected signal-to-noise ratio of the units of the new treatment group and the units of the new control group;

accepting, by the computer, the new treatment group and the new control group only in response to the calculated expected signal-to-noise ratio exceeding a specific threshold value;

recording, by the computer, mean of the new control group, mean of the new treatment group, pairwise standard deviation of the new treatment and control groups, and pairwise mean of the new treatment and control groups, calculated based on measured empirical results for the units of the treatment group and for the units of control group against the specific goal over time, measured at the specific subsequent point in time at which the new subset of units was selected from the production set;

performing, by the computer, an additional experiment comprising exposing the units of the new treatment group to a specific treatment and not exposing the units of the new control group to the specific treatment;

calculating, by the computer, an effect of the performed additional experiment as mean difference in measured activity between the units of the new treatment group and the units of the new control group after having performed the additional experiment;

recording, by the computer, the calculated effect of the performed additional experiment; and calculating, by the computer, a revised optimal sample size to use for subsequent experiments targeting units having the specific static criteria, according to the specific sample size calculation rule set taking into account target effect of the performed additional experiment and an updated expected signal-to-noise ratio, wherein the updated expected signal-to-noise ratio is calculated based on measured empirical results for the units of the new treatment group and for the units of the new control group against the specific goal over time, measured at a second subsequent specific point in time occurring after the performing of the additional experiment.

3. The method of claim 2 further comprising:

refining the target effect as subsequent effective experiments are performed in subsequent passes.

4. The method of claim 1 wherein performing, by the computer, a paired comparison test on the treatment group and the control group further comprises:

iteratively discarding matched pairs to lower the mean percentage difference between the treatment group and the control group.

5. The method of claim 1 further comprising:

automatically segmenting the subset of units into at least two separate subgroups, based on distribution of the units in the subset;

performing a separate experiment on each subgroup; and choosing a given subgroup that achieves a highest average power across all subset experiments.

6. The method of claim 1 wherein:

units comprise people with mobile phones;

treatments comprise text messages;

the specific static criteria comprises people having specific demographic criteria; and the goal comprises increasing a number of transactions executed.

7. The method of claim 1 further comprising:

outputting the calculated optimal sample size to a treatment optimization component, in order to score and select an optimal treatment targeting units having the specific static criteria treatment.

8. A computer implemented method for scoring and selecting an optimal treatment targeting units having specific static criteria, the method comprising:

receiving, by a computer, an optimal sample size to use for experiments targeting units having the specific static criteria, the optimal sample size having been calculated according to a specific sample size calculation rule set taking into account calculated effect of at least one performed experiment, wherein the units comprise mobile computing devices that are associated with empirically measurable activity, such that the empirically measurable activity can be influenced by using specific treatments mapped to a specific goal, wherein the treatments comprise electronic messages automatically transmitted by a sample size and treatment optimization system to the mobile computing devices;

creating, by the computer, a plurality of group sets from a production set, each group set comprising a treatment group of units having the specific static criteria and a corresponding control group of units having the specific static criteria, each group of units being formed according to the received optimal sample size;

performing, by the computer, a separate experiment using a separate treatment mapped to the specific goal, on each separate one of the group sets, each experiment comprising exposing the units of the given treatment group to a given treatment and not exposing the units of the given control group to the given treatment;

for each separate performed experiment, calculating, by the computer, a score for the corresponding specific treatment, according to a specific score calculation rule set taking into account an actual effect size of a performed experiment utilizing a given treatment, statistical significance of the performed experiment utilizing the given treatment, and a measurement of homogeneity of effect of the performed experiment utilizing a given treatment across the corresponding treatment group; and for each separate treatment, performing, by the computer, an action based on the corresponding calculated score from a group of actions consisting of: 1) responsive to the calculated score for a given treatment being below a specific threshold, discarding the given treatment as being suboptimal; 2) responsive to the score for the given treatment being within a specific range, replicating the given performed experiment utilizing the given treatment to validate effect; and 3) responsive to the score for the given treatment exceeding a specific threshold, adjudicating the given treatment as being optimally effective for units with the specific static criteria, and automatically accepting the specific treatment for production usage.

9. The method of claim 8 wherein creating each group set further comprises:

selecting, by the computer, at a specific point in time, a subset of units of the production set meeting the specific static criteria, the selected subset comprising a given number of units for creating a treatment group and a control group, the given number being informed by the received optimal sample size;

creating, by the computer, a treatment group of units from the subset meeting the specific static criteria and a control group of units from the subset meeting the specific static criteria;

performing, by the computer, a paired comparison test on the treatment group and the control group, wherein the paired comparison test compares empirical results for the units of the treatment group to empirical results for the units of the control group, the empirical results for the units of the treatment group and for the units of the control group being against the specific goal over time, measured at the specific point in time at which the subset of units was selected from the production set;

accepting, by the computer, the treatment group and the control group only in response to a mean percentage difference between the treatment group and the control group being less than a specific threshold value;

calculating, by the computer, expected signal-to-noise ratio of the units of the treatment group and the units of the control group according to the specific signal-to-noise ratio calculation rule set, taking into account empirical results for the units of the treatment group and for the units of the control group against the specific goal over time, measured at the specific point in time at which the subset of units was selected from the production set;

performing, by the computer, a test of the calculated expected signal-to-noise ratio of the units of the treatment group and the units of the control group; and accepting, by the computer, the treatment group and the control group only in response to the calculated expected signal-to-noise ratio exceeding a specific threshold value.

10. The method of claim 8 wherein calculating a score for a performed experiment further comprises:

applying a Bonferroni adjustment to account for multiple pairwise tests taking place.

11. The method of claim 8 wherein calculating a score for a performed experiment further comprises:

measuring the treatment effect homogeneity based on at least one of: skewness of pairwise-differences and kurtosis of pairwise-differences.

12. The method of claim 8 wherein calculating a score for a performed experiment further comprises:

taking into account a number of iterations of the given experiment that have been performed, as a factor indicative of validity.

13. The method of claim 8 wherein replicating a given performed experiment utilizing a given treatment to validate effect responsive to the score for the given treatment being within a specific range further comprises:

performing at least one additional iteration of the performed experiment using the given treatment; and calculating a new score for the performed additional iteration.

14. The method of claim 8 wherein automatically accepting a specific treatment for production usage responsive to the score for the given treatment exceeding a specific threshold further comprises:

automatically releasing the specific treatment into a production environment.

* * * * *

UNITED STATES PATENT AND TRADEMARK OFFICE
CERTIFICATE OF CORRECTION

PATENT NO. : 10,770,179 B2
APPLICATION NO. : 15/442404
DATED : September 8, 2020
INVENTOR(S) : Christopher Benjamin Walker et al.

Page 1 of 1

It is certified that error appears in the above-identified patent and that said Letters Patent is hereby corrected as shown below:

On the Title Page

Item (71) Please replace "Juntos, Inc." with --Juntos Finanzas, Inc.--

Signed and Sealed this
Second Day of November, 2021

Drew Hirshfeld
*Performing the Functions and Duties of the
Under Secretary of Commerce for Intellectual Property and
Director of the United States Patent and Trademark Office*